(12) United States Patent
Ågren

(10) Patent No.: US 7,261,858 B2
(45) Date of Patent: Aug. 28, 2007

(54) DETECTOR ARRANGEMENT WITH ROTARY DRIVE IN AN INSTRUMENT FOR PROCESSING MICROSCALE LIQUID SAMPLE VOLUMES

(75) Inventor: Tomas Ågren, Uppsala (SE)

(73) Assignee: Gyros AB, Uppsala (SE)

( * ) Notice: Subject to any disclaimer, the term of this patent is extended or adjusted under 35 U.S.C. 154(b) by 727 days.

(21) Appl. No.: 10/244,420

(22) Filed: Sep. 17, 2002

(65) Prior Publication Data

US 2003/0082075 A1 May 1, 2003

(30) Foreign Application Priority Data

Sep. 17, 2001 (SE) .................................. 0103109

(51) Int. Cl.
*B04B 13/00* (2006.01)
(52) U.S. Cl. .............................. 422/64; 422/67; 422/72
(58) Field of Classification Search .................. 422/64, 422/67, 72, 68.1, 82.08
See application file for complete search history.

(56) References Cited

U.S. PATENT DOCUMENTS 4,456,581 A 6/1984 Edelmann et al.
4,499,514 A * 2/1985 Yamamiya et al. ...... 360/99.12
5,922,617 A * 7/1999 Wang et al. ................. 436/518
6,143,247 A * 11/2000 Sheppard et al. ............. 422/63

FOREIGN PATENT DOCUMENTS

WO WO97/48095 A1 12/1997
WO WO99/09394 A1 2/1999

* cited by examiner

*Primary Examiner*—Jill Warden
*Assistant Examiner*—Natalia Levkovich
(74) *Attorney, Agent, or Firm*—Birch, Stewart, Kolasch & Birch, LLP

(57) ABSTRACT

The invention relates to a detector arrangement in an instrument for analysis of discrete liquid sample volumes in the microliter and/or nanoliter range contained in microchannel structures that are present in a disc shaped microfluidic device. The suggested detector arrangement comprises a detector head, supported to be driven and controlled for linear displacement and positioning in a first radial plane through a central axis of an associated rotary drive. A rotary member is carried for rotation about said central axis in a second radial plane in parallelism with said first radial plane. A vacuum source is connected with the rotary member and in air flow communication with a planar top surface of the rotary member for a wide area distribution of sub-pressure over said top surface, the rotary member carrying the disc shaped substrate in adhering contact with the top surface for spinning the substrate in equidistant and equiangular relation to the detector head.

9 Claims, 3 Drawing Sheets

DETECTOR ARRANGEMENT WITH ROTARY DRIVE IN AN INSTRUMENT FOR PROCESSING MICROSCALE LIQUID SAMPLE VOLUMES

TECHNICAL FIELD

This invention relates to a detector arrangement with rotary drive in an instrument for analysis of microscale liquid sample volumes, in particular for preparative and analytic purposes, e.g. within fields such as medicine, diagnostics, biochemistry, chemistry, molecular biology, etc. A detector arrangement is contemplated for scanning the liquid sample volumes that are contained in a disc shaped substrate having microfluidic structures formed therein for the flow control of the liquid volumes by centrifugal force. More specifically, the invention relates to a detector arrangement wherein scanning is performed while spinning the disc in equidistant and equiangular relation with a detector means in an instrument that is designed for parallel analysis of discrete liquid sample volumes in the microliter and/or nanoliter range.

BACKGROUND AND PRIOR ART

The disc shaped substrate herein referred to has precisely defined microfluidic structures comprising channels, sample basins, reaction chambers, hydrophobic passages and/or other valve structures etc., by which unit operations may be integrated to create scaled down laboratory processes. Through a high precision spinning of the disc, hundreds of analysis may be performed in parallel on a microscale. An automated procedure may be obtained in an instrument incorporating facilities for dispensing liquid samples and reagents to the disc, for spinning and stopping the disc in order to control the process and the movement of liquid in the microstructures, for collecting data and for moving the disc between the operational modules of the instrument. The microfluidic structures may be integrally formed in the disc, and preferably the disc is disposable and manufactured by a replication technique from a synthetic material, i.e. through molding, embossing or the like.

As used herein, the terms "microfluidic", "microstructures" etc. contemplate, that a microchannel structure comprises one or more cavities and/or channels that have a depth and/or a width that is $\leq 10^3$ μm, preferably $\leq 10^2$ μm. "Fluidic" in addition means that a liquid transport is taking place in the microchannels. The lower limit for the width/breadth is typically significantly larger than the size of the largest reagents and constituents of aliquots that are to pass through a microchannel. The volumes of microcavities/microchambers are typically $\leq 1000$ nl but may extend into the μl-range such as up to 10 μl or 50 μl. Chambers/cavities directly connected to inlet ports may be considerably larger, e.g. microchambers/microcavities intended for application of sample and/or washing liquids.

The terms "microscale", "microlab" contemplate, that one or more liquid aliquots introduced into a microchannel structure are in the μl-range or smaller, i.e. $\leq 1000$ μl, or in the nl-range such as $\leq 1000$ nl.

The disc comprises covered microchannel structures that are present in a substrate having an axis of symmetry. Each microchannel structure typically is oriented outwards relative to the axis of symmetry with an inlet port at a shorter radial distance from the symmetry axis than a microcavity in which a certain treatment is going to take place, for instance mixing, separation, a chemical reaction, detection etc. There may also be an outlet port for liquid downstream the reaction microcavity. Each microchannel structure may or may not be oriented in a plane perpendicular to the axis of symmetry. By spinning the disc around its axis of symmetry (axis of rotation), a liquid aliquot placed at an inner position, e.g. the inlet port, will be subjected to a centrifugal force driving the liquid outwards, towards and through the microcavity and/or the outlet port for liquids, if present. Vent ports may also be formed and cooperating with liquid flow restrictions in the microchannel structures for controlling the flow direction of liquid aliquots inwards, towards the axis of rotation, through application of centrifugal forces.

According to the invention other forces may also be used for driving liquid flow in this kind of microchannel structures, for instance electrokinetic forces, capillary forces, inertia force other than centrifugal force, over-pressure, etc. This means, for instance, that it is not imperative that the inlet port is at a shorter radial distance from the symmetry axis, than other functional parts of a microchannel structure.

A rotary drive for spinning the disc to create liquid flow in the microfluidic structures is disclosed in a co-pending application titled "ROTARY DRIVE IN AN INSTRUMENT FOR PROCESSING MICROSCALE LIQUID SAMPLE VOLUMES", assigned to the same applicant and filed on the same day as the present application.

A revolving spindle is contemplated for spinning the disc, the disc being carried on a rotary member connected to the spindle. The drive means must satisfy strict demands for an accurate positioning of the disc at a halt and during spinning for sample preparation and sample dispensing, e.g., for detecting and data collection, e.g., and for high speed spinning during processing. For a time effective operation, the disc must be secured on the rotary member under considerable acceleration and retardation loads. In the process step, the disc may be hastily accelerated to speeds up to about 25,000, such as up to about 10,000, revolutions per minute, or above, and hastily decelerated to a halt.

In the detection step the disc is scanned by a detecting means having a capacity for detecting a particular compound or activity in at least a part area of a detection cavity, such as a fluorescence detector, e.g. In consideration of the microscale dimensions and microscale volumes involved, a rotation that is free from warp and in parallelism with the detector means is then of crucial importance for a repeatable and reliable collection of data.

In this context it is a technical problem in the detection step to secure the planarity and a warp free rotation of the disc shaped substrate and its microstructures in parallelism with the detector means. Therefore, and also for reducing the accelerated mass, it is desired to avoid mechanical structures that would be subject to wear and which may also caused damage to the disc at the point of engagement.

Another technical problem related to spinning the disc in the microlab environment is the necessity for avoiding contaminants such as minute particles down to molecular size, that might originate from frictional wear of mechanical arresting means for holding the disc on the spindle.

It is still another technical problem to initially generate a sealed communication between the adhering side of the disc and a vacuum source, if the disc is not plane. Any irregularities or deviations from the planar condition will produce a leak that impairs on the operation of the vacuum fixation of the disc, and must be avoided to achieve the necessary planarity and parallelism with the detector means.

A rotary drive using sub-pressure for holding a recording medium to a revolving turntable is known from U.S. Pat. No.

4,493,072, wherein a sub-pressure is distributed through channels arranged in a geometric pattern over the contact surface of the turntable.

SUMMARY OF THE INVENTION

It is therefore an object of the present invention to provide a detector arrangement comprising a detector means having an associated rotary drive for simultaneously scanning and spinning the liquid sample volumes in equidistant and equiangular rotation relative to the detector means in an instrument for analysis of microscale sample volumes.

It is another object of the present invention to provide a detector arrangement comprising a detector means and an associated rotary drive for simultaneously scanning and spinning a disc shaped substrate carrying the liquid sample volumes in equidistant and equiangular rotation relative to the detector means in an instrument for analysis of microscale sample volumes, wherein sub-pressure is widely distributed over the seating surface of a rotary member on which the disc is seated for rotation about its axis of symmetry.

It is still another object of the present invention to provide a detector arrangement comprising a detector means and an associated rotary drive for simultaneously scanning and spinning the disc that is carrying the liquid sample volumes in equidistant and equiangular rotation relative to the detector means in an instrument for analysis of microscale sample volumes, wherein sub-pressure is widely distributed over the seating surface of a rotary member on which the disc is seated for rotation about its axis of symmetry, and fixation of the disc is accomplished by initially establishing a sealed sub-pressure communication from the vacuum source to the adhering side of the disc through scaling elements having a capacity for absorbing irregularities and deviations from a planar condition of the disc.

These and other objects are met in a detector arrangement structured as defined in the attached set of claims.

Briefly, the invention suggests a detector arrangement in an instrument for analysis of discrete liquid sample volumes in the microliter and/or nanoliter range contained in microchannel structures that are formed in a disc shaped substrate having an axis of symmetry. The suggested detector arrangement comprises a detector head, supported to be driven and controlled for linear displacement and positioning in a first radial plane through a central axis of an associated rotary drive, the rotary drive having a motor and a spindle. A rotary member is carried on the spindle and driven for rotation about said central axis in a second radial plane in parallelism with said first radial plane, such that each perpendicular to the second plane forms a normal to the first plane. A vacuum source is connected with the rotary member and in air flow communication with a planar top surface of the rotary member for a wide area distribution of sub-pressure over said top surface, the rotary member carrying the disc shaped substrate in adhering contact with the top surface for spinning the substrate about its symmetry axis. Control means serve for positioning of the detector head relative to the symmetry axis for scanning the microcavities that are carried for rotation in equidistant and equiangular relation to the detector head.

A detector arrangement substantially as disclosed herein secures the equidistant and equiangular rotation of the microfluidic disc relative to the detector means for a reliable and repeatable collection of data, indicative for a specific reaction or compound contained in the microcavities of the disc shaped substrate. In this context, the word "equidistant" should be understood to indicate that all detected microscale liquid aliquots contained on the disc shaped substrate are equally distanced from a focal plane of the detector during passage through a detection window or detection area, regardless of their relative position on the substrate. Likewise, "equiangular" indicates that all detected microscale liquid aliquots pass through said window or area at the same vertical angle relative to the focal plane, as measured in a vertical plane through the symmetry axis of the substrate.

Advantageous features and embodiments of the inventive detector arrangement are successively defined in the subordinated claims.

BRIEF DESCRIPTION OF DRAWINGS

The invention is further disclosed below, reference being made to the accompanying drawings. In the drawings.

Features that are described in the context of the embodiments of the drawings are applicable, where appropriate, also to the general innovative embodiment as well as to various other embodiments of the invention.

DETAILED DESCRIPTION OF THE INVENTION

Figure 1:
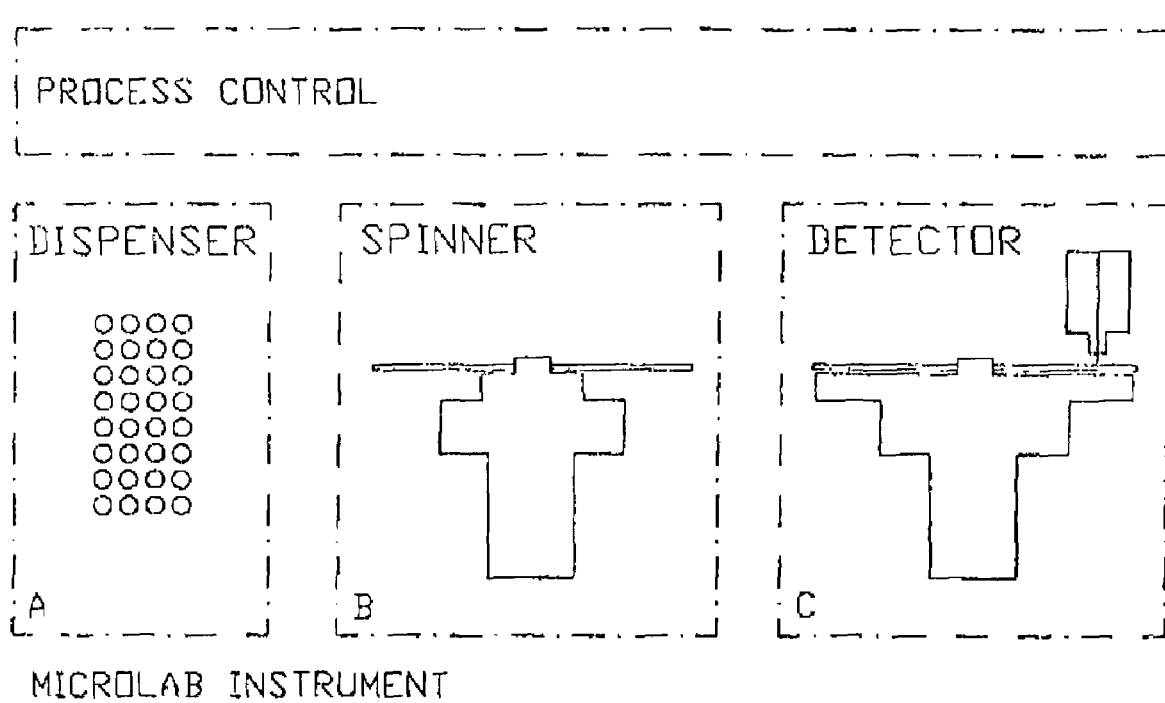
FIG. 1 is a diagrammatic view showing the set up of an instrument for analysis of discrete liquid sample volumes in the microliter or nanoliter range.

An instrument for automated analysis of discrete liquid sample volumes in the microliter or nanoliter scale, as previously discussed, is diagrammatically shown in FIG. 1 to incorporate a sample dispensing station A, a processing station B and a detecting station C. The microlab instrument preferably comprises process control means and mechanics for automated analysis of discrete sample volumes in the microliter and/or nanoliter range.

The discrete liquid sample volumes are contained in a disc shaped substrate having microfluidic structures formed therein for the flow control of microliter and/or nanoliter volumes of liquid by centrifugal force, as previously discussed. The discs are preferably manufactured from plastic material, e.g. by replication techniques, such as embossing, molding, etc. See for instance WO 9116966 (Pharmacia Biotech AB, Öhman & Ekström).

In the microstructure design, unit operations may be integrated to perform scaled down laboratory processes on a disposable disc shaped substrate. In the disc shaped substrate, each microchannel has an inlet port and a microchannel connecting the inlet port with the detection microcavity, preferably with at least two or more of the detection microcavities being at the same radial distance from the symmetry axis of the disc. Through a compact layout of the microstructures and a high precision spinning of the disc, hundreds of analysis may be controlled and processed in parallel on a microscale.

Figure 2:
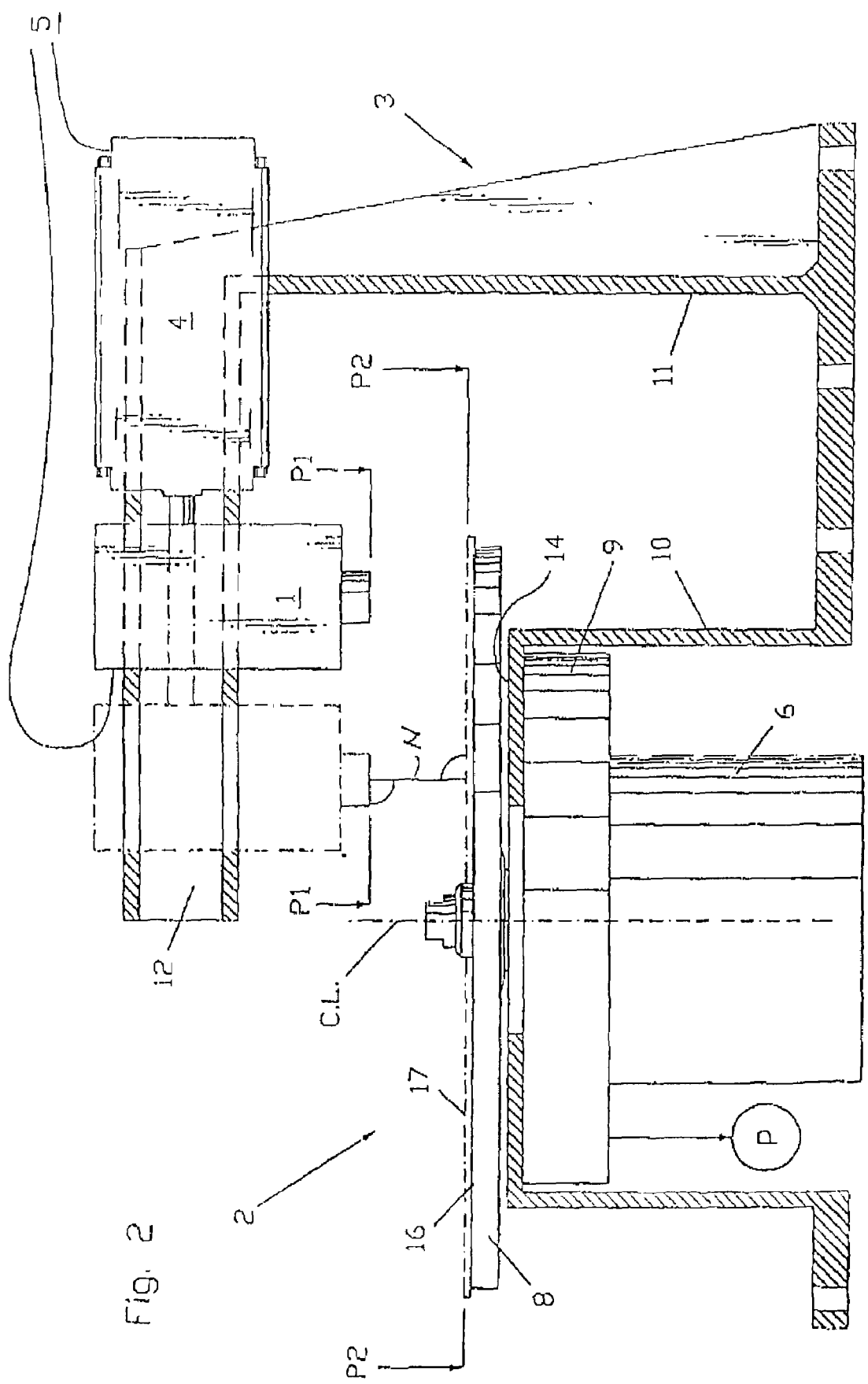
FIG. 2 is a diagrammatic view showing the inventive detector arrangement incorporated in the instrument of FIG. 1.

With reference to FIG. 2, the detector arrangement is diagrammatically illustrated to incorporate a detector head 1 and an associated rotary drive 2 that is contemplated for spinning the disc shaped substrate relative to the detector head in a data collection procedure.

The detector head 1 is equipped to have a capacity for detecting a particular compound or activity in at least a part area of a detection microcavity, formed in the disc shaped substrate. The detector head 1 may be equipped with a photomultiplier for detecting fluorescence or chemiluminiscence, e.g., or be equipped with any suitable detecting means that is adapted for monitoring and/or recording an activity, taking place in the microcavity. A laser induced fluorescence detector may thus be applied for collecting radiation from said partial area of the microcavity, the radiation being indicative of the presence of said compound or activity. The detector head 1 is supported on a frame structure 3 that is mechanically connected with the rotary drive 2 as is further explained below. The detector head 1 is controlled and guided on the frame structure 3 for linear displacement and positioning in a first plane $P_1$, transversely through a central axis CL of the associated rotary drive 2 and running in a radial direction thereto. A drive unit 4 is operable for incrementally changing the position of the detector head 1 in said first radial plane $P_1$ for successively scanning radially adjacent portions of each microcavity arranged on the spinning disc. The vertical height of plane $P_1$ may be adjustable for focusing purposes, e.g.

Electronic and programmable control means (schematically illustrated by reference numeral 5) with operator's interface and software, not further disclosed, is assigned to the detector arrangement for recognizing a start/stop-position, for identifying individual detection microcavities, for controlling the simultaneous rotating of the disc and the incremental displacement of the detector head 1, for collecting data from the microcavity/microcavities, and for treatment and presentation of the collected data, e.g.

The rotary drive 2 of the detector arrangement is more closely explained with reference to FIGS. 2 and 3. A motor 6 has a spindle 7 for spinning a rotary member 8 relative to a stationary member 9. Stationary member 9 is supported from the frame 3 so as to be mechanically connected with the detector head 1. Frame 3 is structurally dimensioned to secure mechanical integrity between detector head 1 and stationary member 9, and comprises a drive mount 10, an upright post 11 and a horizontal arm 12. The drive mount 10, post 11 and arm 12 may be integrally formed, or assembled to form an integral structure. Frame 3 is adapted to be incorporated in the microlab instrument, such as by bolting the frame to an instrument bottom. Stationary member 9 has a plane upper surface that is bolted (13) to a horizontal section 14 of the frame 3, in parallel with the horizontal arm 12 on which the detector head 1 and linear drive 4 are supported. Advantageously, the upper surface of stationary member 9 is centrally formed with a raised shoulder that is frictionally received in a recess, formed in the frame section 14. The motor 6 is bolted (15) and suspended from the stationary member 9, the spindle 7 projecting through the stationary member and non-rotationally connected with the rotary member. Rotary member 8 is formed with a top plane 16 for receiving the disc 17 (illustrated by dash-dot lines in FIG. 2) in adhering contact with the rotary member as is further described below.

Figure 3:
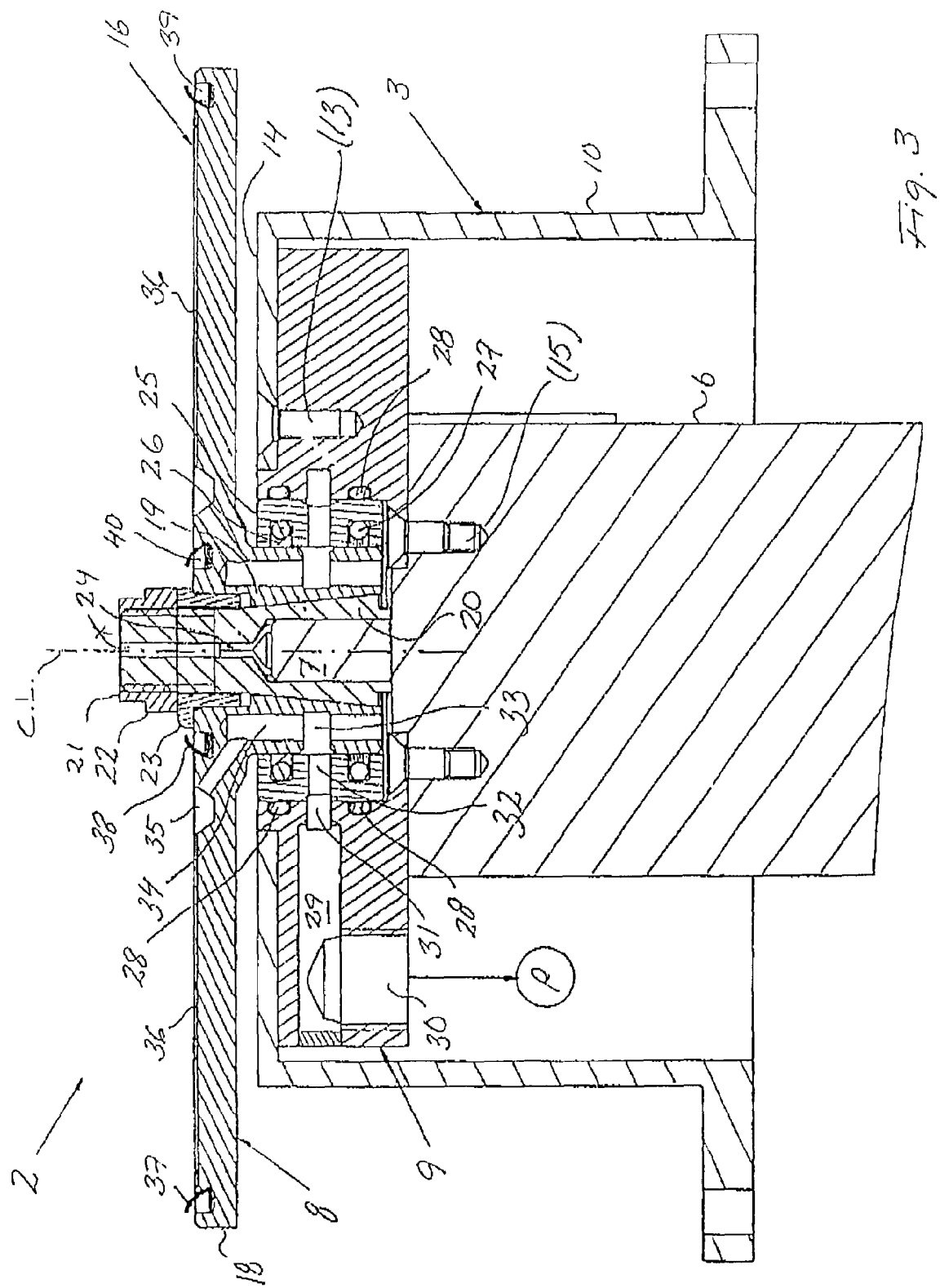
FIG. 3 is a longitudinal section, specifically showing the detailed structure of a rotary drive incorporated in the detector arrangement of FIG. 2 for spinning the sample volumes relative to a detector means.

The rotary member 8 comprises a circular disc 18, the top plane 16 being formed on an upper side thereof and a central hub portion 19 depending from the lower side, as is best seen in FIG. 3. The hub 19 is non-rotationally secured to the spindle 7 by frictionally engaging a tapered sleeve 20 that is caused to be clamped about the spindle upon tightening of a nut 21 in threaded engagement with a cylindrical end portion of the tapered sleeve 20. The nut 21 has a radial shoulder 22 that engages a center guide 23 of the rotary member 8 and, when tightened, urges the rotary member into frictional engagement with the tapered sleeve. The sleeve 20 is radially contracting through two or more longitudinal slots 24 that reach from the lowermost end of the sleeve to terminate above the outer end of spindle 7 in a clamped position about the spindle.

The hub portion is journalled in the stationary member through annular seals in sliding contact with an outer, and cylindrical surface of the hub portion and non-rotationally are seated in the stationary member. The annular seals may be arranged with an axial gap that axially defines a sub-pressure communication between the stationary member and the rotary member. For example, the rotary member 8 is journalled in the stationary member 9 through an intermediate bearing insert 25. Bearing insert 25 is circular in shape and concentrically arranged about the hub portion 19 and the common axis CL. The bearing insert 25 carries a couple of ring shaped slide seals 26, received in annular recesses that are formed in axially spaced relationship on the inner periphery of the insert. Advantageously, the slide seals 26 are biased for an airtight, sliding contact with an outer periphery of the hub 19 by means of ring-shaped springs 27. The bearing insert is frictionally seated in a circular through hole formed in the stationary member 9. Resilient 0-ring seals 28 are seated in the stationary member and axially spaced for an airtight connection between the stationary member 9 and the bearing insert 25.

The disc 18 of rotary member 8 is carefully balanced for a warp free rotation about axis of rotation CL. The disc has a radius that is adapted to the radius of the disc shaped microfluidic substrate 17, and is preferably dimensioned to provide substantially a full area support of the seated microfluidic disc in the detection process. As will be explained below, sub-pressure is widely distributed over the top plane 16 of disc 18 for a wide area adhesion of the microfluidic disc when the disc is spinned in a second plane $P_2$, transversely through said central axis CL of the rotary drive 2 and running in a radial direction thereto. From the disclosure given herein it will be understood, that in the detector arrangement as suggested, each perpendicular to the second plane $P_2$ forms a normal N to the first plane $P_1$.

A vacuum source p (diagrammatically illustrated) is connected with the stationary member 9 and communicating with the top plane 16 for applying sub-pressure to the microfluidic disc. Stationary member 9 is formed with an air duct 29, connected with the vacuum source through connection 30 and mouthing in an annular groove 31 that runs horizontally about the inner periphery of the through hole of stationary member 9. The groove 31 has a radial dimension and an axial width that is defined between the resilient O-ring seals 28. Radial bores 32 are formed through the wall of bearing insert 25 and angularly spaced for communicating the annular groove 31 of stationary member 9 with an annular recess 33 that opens circumferentially in the outer periphery of hub portion 19. The annular recess 33 reaches radially inwards and connects to a number of axially running channels 34, arranged in the depending wall of hub portion 19. The axial channels 34 are angularly spaced in a radial plane and mouthing in the top plane 16, more specifically in a circular groove 35 that opens in the top plane at a radial distance outwardly and about the centering guide 23. A sub-pressure communication is thus established from the vacuum source p, via connection 30, air duct 29, annular groove 31, radial bores 32, annular recess 33, channels 34, and circular groove 35 to the top plane 16.

The top plane 16 is machined to have a highly controlled, general planarity. Sub-pressure is widely distributed over the top plane through shallow formations arranged in the surface of top plane 16. The formations are intended and dimensioned for supporting a percolating air flow that secures a full area adhesion of the microfluidic disc to the top plane 16, such that any irregularities and deviations from the planar condition of the spinning disc thereby are avoided in the detection procedure. Such formations may include indentations and/or impressions and/or channels 36 for distributing sub-pressure outwardly from the circular groove 35, the formations generally having a radial main orientation in the top plane. The channels/impressions/indentations may be straight, curved or angularly changing direction in an organized or randomized pattern in the surface of top plane 16. Other contemplated formations may include a surface texture obtained in a grinding process, or a lightly blasted surface obtained by glass or sand blasting, e.g. Channels, impressions and textures may also be combined, if appropriate. In all embodiments, a peripherally outermost portion of the top plane surface is left untreated for a sealing contact with the lower side of the adhering microfluidic disc in its seated position.

Initially, sub-pressure is applied to the disc shaped substrate by bringing the adhering side of the disc in sealing contact with a peripherally outer and a peripherally inner resilient ring element 37 and 38, respectively. The resilient ring elements 37, 38 project above the top plane surface, supported in circular grooves 39, 40 and are allowed to fully retract in the grooves, below or at level with the top surface when the disc is finally seated in adhering contact with the top plane surface of the rotary member 8. Alternatively, one or both of the resilient rings 37, 38 may be omitted and the disc being placed directly on the top plane 16 of rotary member 8.

Modifications are possible without departing from the teachings advised herein. The appended claims should however be construed to incorporate any and all of such modifications to the invention, that will become apparent for the man of ordinary skill in this art when studying the disclosure given herein.

The invention claimed is:

1. A detector arrangement in an instrument for analysis of discrete liquid sample volumes in the microliter and/or nanoliter range contained in detection microcavities of microchannel structures that are present in a disc shaped substrate having an axis of symmetry perpendicular to the plane of the disc, the detector arrangement comprising:
   a rotary drive having a motor and a spindle;
   a rotary member carried on the spindle and driven for rotation about a central axis in a second plane;
   a detector disposed so as to move linearly in a line through a central axis of the rotary drive in a first plane which is in parallelism with the second plane, such that each perpendicular to the second plane forms a normal to the first plane; and
   a vacuum source connected with the rotary member and in air flow communication with a planar top surface of the rotary member through a plurality of channels for distribution of sub-pressure over said top surface, the rotary member carrying the disc shaped substrate in adhering contact with the top surface for spinning the shaped substrate about a symmetry axis of the disc shaped substrate.

2. The detector arrangement of claim 1 further comprising a detector head and a drive unit, wherein
   the detector head is connected to the drive unit, and the drive unit is powered and change the position of the detector head in the first plane so as to successively scann radially adjacent portions of each microactivity in equidistant and equiangular rotation relative to the detector head.

3. The detector arrangement of claim 2, wherein the detector head comprises a photo-multiplier for detecting chemiluminescence.

4. The detector arrangement of claim 2, wherein the detector head is supported on a frame structure that is mechanically connected with a stationary member of the rotary drive, and the motor is suspended from the stationary member.

5. The detector arrangement of claim 4, further comprising a tapered clamping sleeve, wherein
   the rotary member has a central hub,
   the spindle projects through the stationary member, and the rotary member is journalled in the stationary member through a hub portion of the rotary member, and
   the central hub is connected to the spindle via the tapered clamping sleeve by means of friction between an inner conical surface of the central hub and the tapered clamping sleeve.

6. The detector arrangement of claim 1, wherein the sub-pressure is evenly distributed to the disc shaped substrate through an indentation, an impression or a channel which is arranged in the top surface of the rotary member and in substantially radial direction relative to the central axis.

7. The detector arrangement of claim 6 wherein the indentation, the impression or the channel is designed for establishing a percolating air flow between the disc shaped substrate and the top surface of the rotary member for a full area adhesion of the disc.

8. The detector arrangement of claim 1, further comprising a peripherally outer and a peripherally inner resilient ring, wherein
   the peripherally outer and the peripherally inner resilient ring are on the top surface of the rotary member so as to project above the top surface and fully retract below or to level with the top surface when the sub-pressure communication from the vacuum source to the adhering side of the disc shaped substrate is carried out.

9. The detector arrangement of claim 1, further comprising a control means for positioning the detector, wherein
   the control means for positioning the detector can change a position of the detector so that the detector pass a detection window in equidistant and equiangular relation to a focal plane of the detector and scan the microcavities.

* * * * *